(12) United States Patent
Matsuura

(10) Patent No.: US 8,340,383 B2
(45) Date of Patent: Dec. 25, 2012

(54) CT SCANNER AND CONTROL METHOD THEREFOR

(75) Inventor: Tomohiko Matsuura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 841 days.

(21) Appl. No.: 12/184,635

(22) Filed: Aug. 1, 2008

(65) Prior Publication Data
US 2009/0046916 A1    Feb. 19, 2009

(30) Foreign Application Priority Data
Aug. 13, 2007    (JP) ................................. 2007-211058

(51) Int. Cl.
*A61B 6/00* (2006.01)
*G06K 9/00* (2006.01)
*G01D 18/00* (2006.01)

(52) U.S. Cl. ........................... 382/131; 378/19; 378/207

(58) Field of Classification Search .................. 382/128, 382/130, 131, 132; 378/4, 19, 901, 207
See application file for complete search history.

(56) References Cited

U.S. PATENT DOCUMENTS

| | | | |
|---|---|---|---|
| 6,229,869 B1 | 5/2001 | Hu | |
| 6,325,539 B1 * | 12/2001 | Bromberg et al. | 378/207 |
| 6,510,241 B1 * | 1/2003 | Vaillant et al. | 382/154 |
| 7,327,823 B2 | 2/2008 | Matsuura | 378/8 |
| 7,760,852 B2 * | 7/2010 | Chen et al. | 378/19 |
| 2007/0122020 A1 * | 5/2007 | Claus et al. | 382/131 |
| 2009/0262886 A1 * | 10/2009 | Mollus et al. | 378/19 |

FOREIGN PATENT DOCUMENTS

| | | |
|---|---|---|
| JP | 2000-083947 A | 3/2000 |
| JP | 2005-058758 | 3/2005 |
| JP | 3698167 B2 | 9/2005 |
| JP | 2005-296340 | 10/2005 |
| JP | 2006-288719 | 10/2006 |
| JP | 3846577 B2 | 11/2006 |

OTHER PUBLICATIONS

Office Action dated Jun. 22, 2012, issued in counterpart Japanese Patent Application No. 2007-211058, with English summary (above).

* cited by examiner

*Primary Examiner* — Irakli Kiknadze
(74) *Attorney, Agent, or Firm* — Fitzpatrick, Cella, Harper & Scinto

(57) ABSTRACT

A CT scanner which can reconstruct high-quality tomographic images using only the projected images obtained by scanning an object without requiring any special three-dimensional phantom is provided. A two-dimensional radiation sensor placed to face a radiation source via the object acquires projected images while relatively rotating the object in the radiation emitted from the radiation source. Tomographic images are obtained at one predetermined slice position of the object by performing, for each of geometrical calibration parameter values, reconstruction of a tomographic image of the object using one of the calibration parameter values based on acquired projected images. One of the calibration parameter values is selected based on the obtained tomographic images. A tomographic image is reconstructed at each slice position by using a selected calibration parameter value based on a projected image at each acquired slice position of the object.

16 Claims, 4 Drawing Sheets

CT SCANNER AND CONTROL METHOD THEREFOR

BACKGROUND OF THE INVENTION

1. Field of the Invention

The present invention relates to a CT (Computed Tomography) scanner which obtains tomographic images by CT reconstruction, and a control method for the scanner.

2. Description of the Related Art

In general, in a CT scanner, a radiation source and a two-dimensional radiation sensor are placed to face each other through an object, and the object is relatively rotated in the radiation emitted from the radiation source. The scanner obtains tomographic images of the object by performing CT reconstruction of projected images of the object which are obtained from various directions during this rotation.

This CT reconstruction requires parameters associated with the position and tilt of the rotation axis of the object relative to the radiation source and the two-dimensional radiation sensor. The scanner cannot obtain high-quality tomographic images without accurately grasping these parameters.

Under the circumstance, as a method of estimating the relative position and tilt of the rotation axis of an object, there is known a method of performing estimation by using a three-dimensional phantom which has a series of cell structures and whose dimension is known in advance based on projected images obtained by CT-scanning the three-dimensional phantom (see Japanese Patent No. 3698167). There is also known a method of performing estimation by generating sinograms from projected images obtained by CT-scanning an object and using the symmetry of the sinograms (see Japanese Patent No. 3846577).

The method using a three-dimensional phantom, however, requires a special three-dimensional phantom, and hence requires scanning of the three-dimensional phantom independently of scanning of the object. In addition, there is no guarantee that the position and tilt of the rotation axis of the object at the time of scanning will perfectly coincide with those of the three-dimensional phantom at the time of scanning. Furthermore, the manufacturing accuracy of a three-dimensional phantom may affect the estimation accuracy of optimal parameters.

The method using sinograms is designed to estimate optimal parameters in the coordinate system of a projected image. It is possible that an estimation error may affect the quality of a tomographic image after reconstruction.

SUMMARY OF THE INVENTION

It is, therefore, an object of the present invention to provide a CT scanning technique which can accurately estimate the relative position and tilt of the rotation axis of an object by using only projected images obtained by scanning the object without requiring any special three-dimensional phantom and finally obtain high-quality tomographic images.

According to one aspect of the present invention, a CT scanner comprises an acquisition unit configured to acquire a projected image by using a two-dimensional radiation sensor placed to face a radiation source through an object while relatively rotating the object in radiation emitted from the radiation source, a first reconstruction unit configured to obtain a plurality of tomographic images at one predetermined slice position of the object by performing, for each of a plurality of geometrical calibration parameter values, reconstruction of a tomographic image of the object using one of the plurality of geometrical calibration parameter values based on a projected image acquired by the acquisition unit, a selection unit configured to select one of the plurality of geometrical calibration parameter values based on the plurality of tomographic images obtained by the first reconstruction unit, and a second reconstruction unit configured to reconstruct a tomographic image at each slice position of the object by using a geometrical calibration parameter value selected by the selection unit based on a projected image at each slice position which is acquired by the acquisition unit.

Further features and aspects of the present invention will become apparent from the following description of exemplary embodiments with reference to the attached drawings.

DESCRIPTION OF THE EMBODIMENTS

Various exemplary embodiments, features, and aspects of the present invention will be described in detail below with reference to the drawings.

(First Embodiment)

Figure 1:
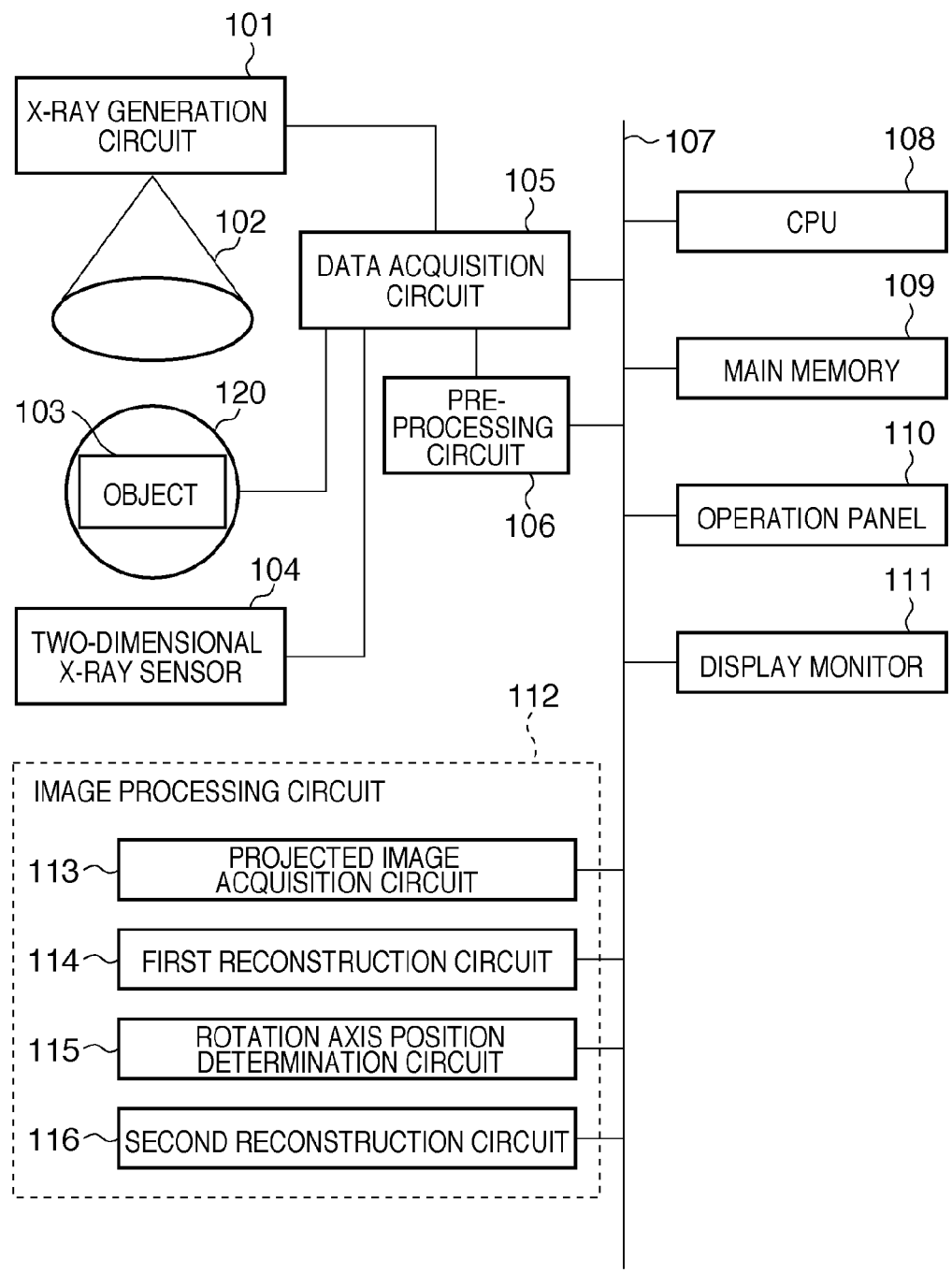
FIG. 1 is a block diagram showing the arrangement of a CT scanner according to an embodiment.

FIG. 1 is a block diagram showing the arrangement of a CT scanner 100 according to this embodiment. The CT scanner 100 according to this embodiment is a CT scanner which has a function of determining the position of the rotation axis of an object. More specifically, this scanner comprises a preprocessing circuit 106, a CPU 108, a main memory 109, an operation panel 110, a display monitor 111, and an image processing circuit 112, which exchange data with each other via a bus 107.

A data acquisition circuit 105 is connected to the preprocessing circuit 106. An X-ray generation circuit 101 which is a radiation source, a rotation unit 120 which rotates an object 103, and a two-dimensional X-ray sensor 104 as a two-dimensional radiation sensor are connected to the data acquisition circuit 105. The data acquisition circuit 105 is connected to the bus 107. The X-ray generation circuit 101 and the two-dimensional X-ray sensor 104 are placed to face each other through the object 103.

The main memory 109 stores various data and the like necessary for processing by the CPU 108, and includes a work memory for operation by the CPU 108. The CPU 108 performs, for example, operation control on the overall scanner in accordance with operation from the operation panel 110 using the main memory 109. More specifically, the CT scanner 100 operates in the following manner.

First of all, the rotation unit 120 is activated to rotate the object 103. The X-ray generation circuit 101 then applies an X-ray beam 102 to the object 103. The X-ray beam 102 applied from the X-ray generation circuit 101 is transmitted through the object 103 while being attenuated, and reaches the two-dimensional X-ray sensor 104. The two-dimensional X-ray sensor 104 then outputs the X-ray beam as scanned data.

The data acquisition circuit 105 converts the scanned data output from the two-dimensional X-ray sensor 104 into an electrical signal and supplies it to the pre-processing circuit 106. The pre-processing circuit 106 performs pre-processing such as offset correction or gain correction for a scanned data signal from the data acquisition circuit 105. The scanned data signal pre-processed by the pre-processing circuit 106 is transferred as a projected image to the main memory 109 and the image processing circuit 112 via the bus 107 under the control of the CPU 108. In this embodiment, the two-dimensional X-ray sensor 104, the data acquisition circuit 105, and the pre-processing circuit 106 are separately arranged. However, the two-dimensional X-ray sensor 104, the data acquisition circuit 105, and the pre-processing circuit 106 can be arranged in the same unit as a sensor unit.

The CPU 108 activates the rotation unit 120 and controls the X-ray generation circuit 101 to continuously or discontinuously apply the X-ray beam 102 while rotating the object 103. In this operation state, that is, CT scanning state, the two-dimensional X-ray sensor 104 sequentially acquires scanned data, and sequentially sends the acquired scanned data to the data acquisition circuit 105. For example, the two-dimensional X-ray sensor 104 acquires 1,000 scanned data while the object 103 rotates once, and transfers the data to the data acquisition circuit 105. The data acquisition circuit 105 transfers scanned data signals to the pre-processing circuit 106. The pre-processing circuit 106 performs the above processing and transfers the resultant projected images to the image processing circuit 112 and the main memory 109. With the above scanning operation, the projected images obtained by scanning the object 103 from various directions are sequentially transferred to the image processing circuit 112. At the same time, the projected images are transferred to and stored in the main memory 109.

As shown in FIG. 1, the image processing circuit 112 comprises a projected image acquisition circuit 113, a first reconstruction circuit 114, a rotation axis position determination circuit 115, and a second reconstruction circuit 116. The projected image acquisition circuit 113 sequentially acquires the projected images processed by the pre-processing circuit 106 during CT scanning. The first reconstruction circuit 114 performs CT reconstruction for calibration by using the acquired projected images. The rotation axis position determination circuit 115 determines the position of the rotation axis of the object based on a plurality of tomographic images for calibration. The second reconstruction circuit 116 performs final CT reconstruction by using the determined rotation axis position.

Figure 2:
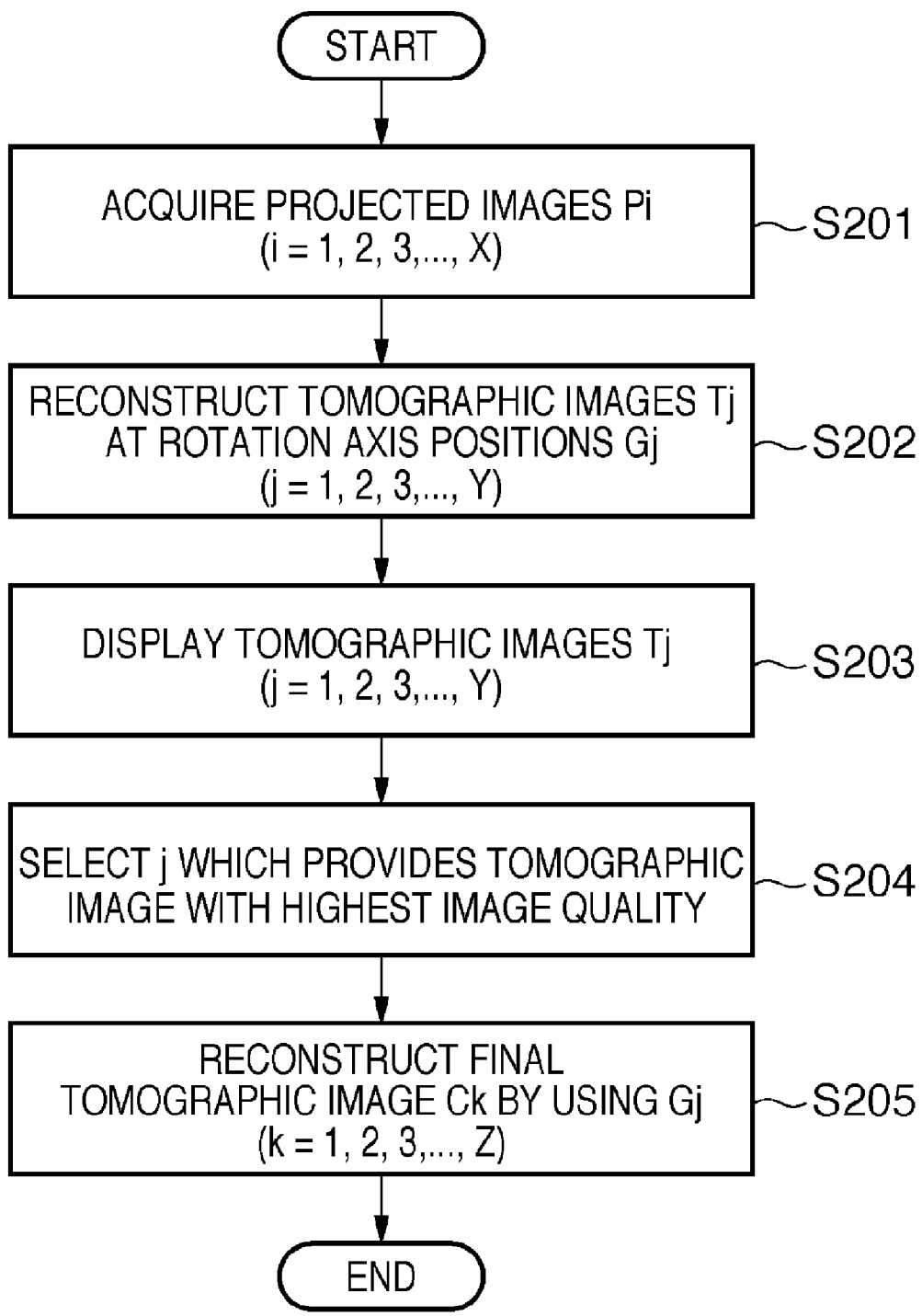
FIG. 2 is a flowchart showing the procedure of processing in an image processing circuit according to the first embodiment.
Figure 3:
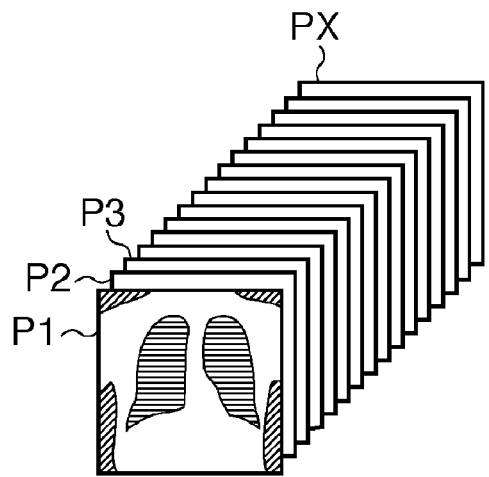
FIG. 3 is a view showing projected images obtained by scanning from different directions, which are sequentially acquired during CT scanning.
Figure 4:
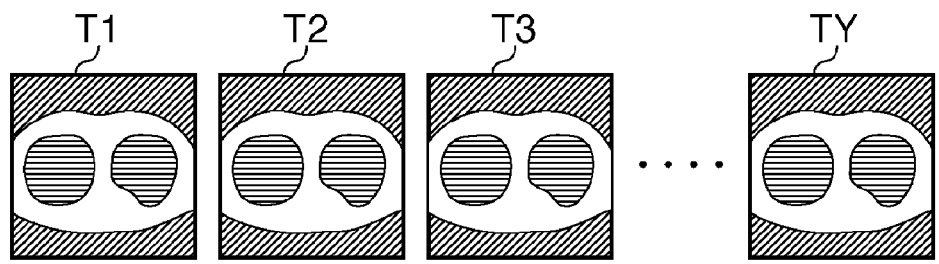
FIG. 4 is a view showing tomographic images for calibration which are reconstructed by a first reconstruction circuit.
Figure 5:
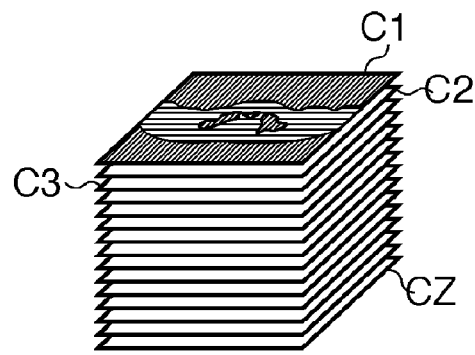
FIG. 5 is a view showing final tomographic images reconstructed by a second reconstruction circuit.

FIG. 2 is a flowchart showing the procedure of processing in the image processing circuit 112 in this embodiment. FIG. 3 is a view showing projected images Pi (i=1 to X) sequentially obtained by scanning from different directions during CT scanning. FIG. 4 is a view showing tomographic images Tj (j=1 to Y) for calibration which are reconstructed by the first reconstruction circuit 114. FIG. 5 is a view showing final tomographic images Ck (k=1 to Z) reconstructed by the second reconstruction circuit 116. Note that the program based on the flowchart shown in FIG. 2 is stored in the main memory 109 or a ROM (not shown), and is read out and executed by the CPU 108.

The operation of the image processing circuit 112 will be described below with reference to the flowchart of FIG. 2.

First of all, the projected image acquisition circuit 113 sequentially acquires, via the bus 107, the projected images Pi (i=1 to X) at one predetermined slice position which are processed by the pre-processing circuit 106 (step S201).

The first reconstruction circuit 114 reconstructs the tomographic images Tj (j=1 to Y) for calibration from the projected images Pi (i=1 to X) (step S202). The first reconstruction circuit 114 performs CT reconstruction Y times upon setting parameter values Gj (j=1 to Y) associated with the rotation axis position as a plurality of different geometrical calibration parameter values, and outputs a plurality of tomographic images Tj for calibration which correspond to the respective values Gj. In this case, "the parameters associated with the rotation axis position" are the parameters of the position of the rotation axis of the object 103 relative to the X-ray generation circuit 101 and the two-dimensional X-ray sensor 104. The minimum interval of Gj is preferably a sufficiently small value relative to the resolution of projected images and/or tomographic images, and is set to, for example, 50 µm. In addition, Y needs to be set based on the allowable range of rotation axis positions, and is set as, for example, Y=100. In this case, the allowable range of rotation axis positions for setting 100 values Gj at intervals of 50 µm is 5 mm. It is possible to determine optimal parameters within this range.

The rotation axis position determination circuit 115 then displays the plurality of tomographic images Tj (j=1 to Y) for calibration on the display monitor 111 (step S203). In this case, the user designates the tomographic images Tj (j=1 to Y) for calibration, of the plurality of tomographic images for calibration displayed on the display monitor 111, which are determined as having highest image quality, by using the operation panel 110. The rotation axis position determination circuit 115 selects, as optimal parameter values, parameters Gj associated with the rotation axis position which have been used when the designated tomographic images Tj have been reconstructed in step S202 (step S204).

The second reconstruction circuit 116 reconstructs final tomographic images Ck from the projected images Pi (i=1 to X) at slice positions k (k=1 to Z) by using the optimal parameter values Gj associated with the rotation axis position which are selected in step S204 (step S205).

In this embodiment, parameters associated with the position of the rotation axis are handled. However, it is possible to determine optimal parameter values of parameters associated with the tilt of the rotation axis by the same processing. In this case, "parameters associated with the tilt of the rotation axis" are parameters of the tilt of the rotation axis of the object 103 relative to the X-ray generation circuit 101 and the two-dimensional X-ray sensor 104. If, for example, the minimum interval of the values Gj is set to 0.1°, i.e., Y=50, the allowable range of rotation axis tilts is 5°. It is possible to determine optimal parameters within this range. In addition, it is possible to simultaneously determine optimal parameters associated with the position and tilt of the rotation axis by variously changing the combination of parameters.

In addition, in this embodiment, the projected image acquisition unit is configured to rotate the object 103 by using the rotation unit 120. However, the same effect can obviously be obtained by integrally rotating the X-ray generation circuit 101 and a two-dimensional X-ray sensor around the object 103. That is, the projected image acquisition unit of the present invention includes a unit which acquires projected images by using the two-dimensional radiation sensor placed to face the radiation source through the object while relatively rotating the object in the radiation emitted from the radiation source.

As described above, this embodiment has the effect capable of accurately estimating the relative position and/or tilt of the rotation axis of an object by using only projected images obtained by scanning the object without requiring any special three-dimensional phantom. This makes it possible to finally obtain high-quality tomographic images.

(Second Embodiment)

This embodiment also uses a CT scanner 100 having the same arrangement (FIG. 1) as that of the first embodiment described above. However, this embodiment differs from the first embodiment in the functions of a first reconstruction circuit 114 and rotation axis position determination circuit 115 of an image processing circuit 112. Therefore, portions associated with these circuits will mainly be described below.

Figure 6:
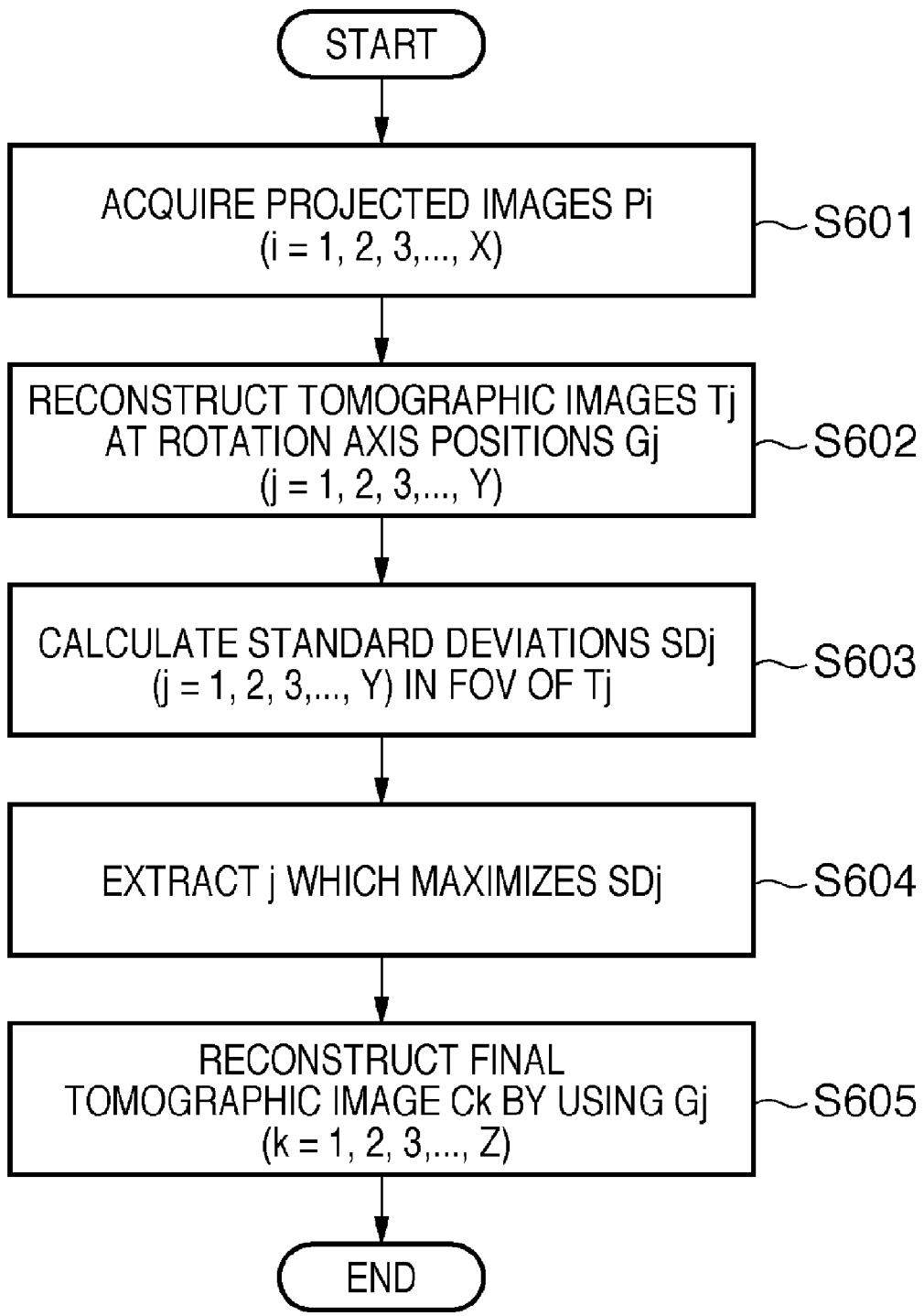
FIG. 6 is a flowchart showing the procedure of processing in a second image processing circuit in the second embodiment.

FIG. 6 is a flowchart showing the procedure of processing in the image processing circuit 112 in this embodiment.

With the same CT scanning operation as in the first embodiment, the projected images obtained by scanning an object 103 at a predetermined slice position from various directions are transferred to the image processing circuit 112 (step S601).

The first reconstruction circuit 114 performs CT reconstruction Y times by using values Gj (j=1 to Y) of parameters associated with a plurality of different rotation axis positions to obtain tomographic images Tj for calibration corresponding to the values Gj (step S602). The first reconstruction circuit 114 performs CT reconstruction by using partial projected images, for example, every 10 projected images P1, P11, P21, ..., PX', instead of using all projected images Pi (i=1 to X). This makes it possible to shorten the processing time as compared with the processing (step S202) by the first reconstruction circuit 114 in the first embodiment.

The rotation axis position determination circuit 115 then calculates standard deviations SDj (j=1 to Y) in the effective fields of view (FOV) of tomographic images Tj (j=1 to Y) for calibration (step S603). Thereafter, the rotation axis position determination circuit 115 extracts j which maximizes SDj (j=1 to Y), and automatically selects a value Gj of a parameter associated with the rotation axis position which corresponds to the extracted value j as an optimal parameter value (step S604). This operation uses a characteristic that the amount of blur of a reconstructed tomographic image increases with an increase in the difference between a rotation axis position used for reconstruction and a true rotation axis position according to the principle of CT reconstruction. In other words, a rotation axis position at which the amount of blur becomes minimum can be regarded as a position nearest to the true rotation axis position. Although various methods of evaluating the amount of blur are conceivable, this embodiment uses a standard deviation in an effective field of view (FOV).

A second reconstruction circuit 116 then reconstructs final tomographic images Ck from projected images Pi (i=1 to X) at slice positions k (k=1 to Z) by using optimal values Gj of parameters associated with the rotation axis position determined in step S604 (step S605).

As described above, according to this embodiment, the relative position and/or tilt of the rotation axis of an object can be accurately and automatically estimated by using only the projected images obtained by scanning an object without requiring any specific three-dimensional phantom. This makes it possible to finally obtain high-quality tomographic images.

(Other Embodiments)

Note that the present invention can be applied to an apparatus comprising a single device or to system constituted by a plurality of devices.

Furthermore, the invention can be implemented by supplying a software program, which implements the functions of the foregoing embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention can be implemented by a computer, the program code installed in the computer also implements the present invention. In other words, the present invention also covers a computer program for the purpose of implementing the functions of the present invention.

In this case, so long as the system or apparatus has the functions of the program, the program may be executed in any form, such as an object code, a program executed by an interpreter, or script data supplied to an operating system.

Example of storage media that can be used for supplying the program are a floppy disk, a hard disk, an optical disk, a magneto-optical disk, a CD-ROM, a CD-R, a CD-RW, a magnetic tape, a non-volatile type memory card, a ROM, and a DVD (DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functions of the present invention by computer is also covered by the present invention.

It is also possible to encrypt and store the program of the present invention on a storage medium such as a CD-ROM, distribute the storage medium to users, allow users who meet certain requirements to download decryption key information from a website via the Internet, and allow these users to decrypt the encrypted program using the key information, whereby the program is installed in the user computer.

Besides the cases where the aforementioned functions according to the embodiments are implemented by executing the read program by computer, an operating system or the like running on the computer may perform all or a part of the actual processing so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-211058, filed Aug. 13, 2007, which is hereby incorporated by reference herein in its entirety.

What is claimed is:

1. An image processing apparatus comprising:
   an acquisition unit configured to acquire projected images by using a two- dimensional radiation sensor placed to face a radiation source through an object while the two-dimensional radiation sensor and the radiation source are integrally rotating relative to the object and around the object;
   a reconstruction unit configured to reconstruct a plurality of tomographic images of the object from the acquired projected images using a plurality of calibration parameter values;
   a selection unit configured to select at least one of the plurality of calibration parameter values; and
   an output unit configured to output a tomographic image based on the selected at least one of the plurality of calibration parameter values,
   wherein the plurality of calibration parameter values include parameter values of a tilt of a rotation axis of the object relative to the radiation source and the two-dimensional radiation sensor.

2. The image processing apparatus according to claim 1, wherein said selection unit is configured to select the at least one of the plurality of calibration parameter values based on the tomographic images obtained by said reconstruction unit.

3. The image processing apparatus according to claim 2, further comprising a calculation unit configured to calculate an image metric value of the tomographic images,
   wherein said selection unit is configured to select the at least one of the plurality of calibration parameter values based on the image metric value.

4. The image processing apparatus according to claim 3, wherein said calculation unit is configured to calculate an amount of blur of the tomographic images.

5. The image processing apparatus according to claim 3, wherein the image metric value comprises a standard deviation value of the tomographic images.

6. The image processing apparatus according to claim 1, further comprising:
   a display unit configured to display the plurality of tomographic images obtained by said reconstruction unit; and
   a reception unit configured to receive designation of a tomographic image from an operation unit,
   wherein said selection unit is configured to select the at least one of the calibration parameter values to be used in the reconstruction of the designated tomographic image.

7. The image processing apparatus according to claim 1, wherein said reconstruction unit is configured to reconstruct a tomographic image of the object based on a subset of projected images of projected images acquired by said acquisition unit while the radiation source and the two-dimensional radiation sensor are integrally rotating relative to the object and around the object once.

8. The image processing apparatus according to claim 7, wherein said reconstruction unit is configured to reconstruct a tomographic image of the object based on the at least one of the plurality of calibration parameter values selected by said selection unit and a plurality of projected images that are greater in number than the projected images in the subset.

9. The image processing apparatus according to claim 1, wherein said reconstruction unit is configured to reconstruct a tomographic image of the object based on the at least one of the plurality of calibration parameter values selected by said selection unit and the projected image acquired by said acquisition unit.

10. The image processing apparatus according to claim 1, wherein said acquisition unit is configured to acquire the projected images while the object positioned between the two-dimensional radiation sensor and the radiation source is rotating.

11. The image processing apparatus according to claim 1, wherein said acquisition unit is configured to acquire the projected images while the two-dimensional radiation sensor and the radiation source are integrally rotating around the object.

12. A computed tomography scanner comprising:
    an image processing apparatus according to claim 1;
    a radiation source;
    a two-dimensional radiation sensor placed to face said radiation source through an object; and
    a drive unit configured to integrally rotate said radiation sensor and said radiation source relative to the object and around the object.

13. The image processing apparatus according to claim 1, wherein the plurality of calibration parameter values further include parameter values of a position of the rotation axis of the object relative to the radiation source and the two-dimensional radiation sensor,
    and wherein said reconstruction unit is configured to reconstruct the plurality of tomographic images of a predetermined slice position of the object from the acquired projected images using different combinations of one of the parameter values of the position of the rotation axis and one of the parameter values of the tilt of the rotation axis.

14. The image processing apparatus according to claim 1, wherein said reconstruction unit is configured to set the minimum interval of the parameter values of the tilt of the rotation axis and the number of the plurality of tomographic images of the object to be obtained at a predetermined slice position, and to obtain the plurality of tomographic images within the set conditions.

15. An image processing method comprising:
    acquiring projected images by using a two-dimensional radiation sensor placed to face a radiation source through an object while the two-dimensional radiation sensor and the radiation source are integrally rotating relative to the object and around the object;
    reconstructing a plurality of tomographic images of the object from the acquired projected images using a plurality of calibration parameter values;
    selecting at least one of the plurality of the calibration parameter values; and
    outputting a tomographic image based on the selected at least one of the plurality of the calibration parameter values,
    wherein the plurality of calibration parameter values include parameter values of a tilt of a rotation axis of the object relative to the radiation source and the two-dimensional radiation sensor.

16. A non-transitory computer readable medium storing instructions to a processor for image processing, the instructions comprising:
- an instruction to acquire projected images by using a two-dimensional radiation sensor placed to face a radiation source through an object while the two-dimensional radiation sensor and the radiation source are integrally rotating relative to the object and around the object;
- an instruction to reconstruct a plurality of tomographic images of the object from the acquired projected images using a plurality of calibration parameter values;
- an instruction to select at least one of the plurality of the calibration parameter values; and
- an instruction to output a tomographic image based on the selected at least one of the plurality of calibration parameter values,
- wherein the plurality of calibration parameter values include parameter values of a tilt of a rotation axis of the object relative to the radiation source and the two-dimensional radiation sensor.

* * * * *